(12) United States Patent
Hernandez Castaneda et al.

(10) Patent No.: US 11,353,722 B2
(45) Date of Patent: Jun. 7, 2022

(54) METHOD FOR DETERMINING A SPECIFIC NEAR VISION POWER OF AN OPHTHALMIC LENS

(71) Applicant: ESSILOR INTERNATIONAL, Charenton-le-Pont (FR)

(72) Inventors: Martha Hernandez Castaneda, Charenton-le-Pont (FR); Paul Joret, Charenton-le-Pont (FR); Jean-Luc Perrin, Charenton-le-Pont (FR); Cyril Guilloux, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 189 days.

(21) Appl. No.: 16/612,807

(22) PCT Filed: Apr. 30, 2018

(86) PCT No.: PCT/EP2018/061016
§ 371 (c)(1),
(2) Date: Nov. 12, 2019

(87) PCT Pub. No.: WO2018/206336
PCT Pub. Date: Nov. 15, 2018

(65) Prior Publication Data
US 2020/0064657 A1     Feb. 27, 2020

(30) Foreign Application Priority Data

May 12, 2017  (EP) .................................. 17305544

(51) Int. Cl.
*G02C 7/02*     (2006.01)
*G02C 7/06*     (2006.01)
(Continued)

(52) U.S. Cl.
CPC .............. *G02C 7/027* (2013.01); *A61B 3/028* (2013.01); *A61B 3/09* (2013.01); *G02C 7/061* (2013.01)

(58) Field of Classification Search
CPC ........ G02C 7/027; G02C 7/024; G02C 7/028; G02C 7/041; G02C 7/06; G02C 7/061;
(Continued)

(56) References Cited

U.S. PATENT DOCUMENTS 5,861,941 A * 1/1999 Liebers .................... A61B 3/18
                                                          351/245
2008/0143960 A1   6/2008 Macrae
(Continued)

FOREIGN PATENT DOCUMENTS

WO     2017/064060 A1    4/2017

OTHER PUBLICATIONS

International Search Report, dated Aug. 1, 2018, from corresponding PCT application No. PCT/EP2018/061016.

*Primary Examiner* — Jordan M Schwartz
(74) *Attorney, Agent, or Firm* — Nixon & Vanderhye

(57) ABSTRACT

Disclosed is a method for determining a specific near vision power of an ophthalmic lens to be provided to a wearer having an ophthalmic prescription, the specific near vision power being for near distance vision, the method including: an ophthalmic lens providing step during which at least an ophthalmic lens having a near distance vision zone including a mean power adapted for near distance vision is provided to the wearer; a near vision task speed determining step during which the processing speed of a near vision task by the wearer when wearing the provided ophthalmic lens is determined; wherein the ophthalmic lens providing step and the near vision task speed determining step are repeated with ophthalmic lenses having different mean power, so as to
(Continued)

determine a specific near vision power corresponding to the mean power providing an improved near vision task processing speed.

21 Claims, 1 Drawing Sheet

(51) Int. Cl.
*A61B 3/028* (2006.01)
*A61B 3/09* (2006.01)
*A61B 3/04* (2006.01)

(58) Field of Classification Search
CPC .. A61B 3/028; A61B 3/09; A61B 3/04; A61B 3/032
USPC .......................................... 351/222, 227–231
See application file for complete search history.

(56) References Cited

U.S. PATENT DOCUMENTS

| | | |
|---|---|---|
| 2010/0002191 A1 | 1/2010 | Drobe |
| 2012/0194780 A1* | 8/2012 | Back ...................... G02C 7/041 |
| | | 351/159.73 |
| 2012/0273110 A1* | 11/2012 | Harris .............. B29D 11/00913 |
| | | 156/60 |
| 2017/0017083 A1 | 1/2017 | Samec et al. |
| 2017/0119247 A1 | 5/2017 | Walsh et al. |
| 2017/0188813 A1* | 7/2017 | Arnold ................... A61B 3/005 |

* cited by examiner

METHOD FOR DETERMINING A SPECIFIC NEAR VISION POWER OF AN OPHTHALMIC LENS

FIELD OF THE INVENTION

The invention relates to a method for determining a specific near vision power of an ophthalmic lens and an ophthalmic lens ordering method.

BACKGROUND OF THE INVENTION

Usually, a person needing to wear spectacles and having thus a prescription filled by an ophthalmologist or optometrist goes to the shop of an optician. The optician orders a pair of optical lenses corresponding to the prescription of the wearer.

The pair of optical lenses sent to the optician are designed and manufactured according to optical criteria.

Recent improvements in the field of ophthalmic lenses, have allowed providing customized optical lenses, such customization going beyond the wearer's prescription. Further parameters than the wearer's prescription may be considered when designing and manufacturing the pair of ophthalmic lenses.

For example, it is known that individuals may have different propensity to move either their eyes or their head when successively looking in different directions.

Such propensity can be of importance when producing ophthalmic lenses.

As disclosed in US 2010/0002191, such propensity can be taken into account in order to determine a compromise between the correction of the foveal vision and that of the peripheral vision when producing an ophthalmic lens.

However, the near vision power is usually determined based on the far vision power and on empiric data such as the age of the person.

Subjective test may be carried out having the person try different near vision power while seeking at a near distance target. The near vision power is determined based on the preference of the person.

With the improvement of the design and manufacturing method, lens manufacturer may provide more accurate optical lenses. The accuracy of the optical lenses that lens manufacturer may provide is not fully exploited because of the accuracy of the prescription determination methods. In particular, the method for determining the near vision power.

Therefore, there is a need for more accurate method for determining the near vision optical power to be provided to a person.

A goal of the present invention is to provide such a method.

SUMMARY OF THE INVENTION

To this end, the invention proposes a method for determining a specific near vision power of an ophthalmic lens to be provided to a wearer having an ophthalmic prescription, the specific near vision power being for near distance vision, the method comprising:
- an ophthalmic lens providing step during which at least an ophthalmic lens having a near distance vision zone comprising a mean power adapted for near distance vision is provided to the wearer,
- a near vision task speed determining step during which the processing speed of a near vision task by the wearer when wearing said provided ophthalmic lens is determined, wherein the ophthalmic lens providing step and the near vision task speed determining step are repeated with ophthalmic lenses having different mean power, so as to determine a specific near vision power corresponding to the mean power providing an improved near vision task processing speed.

Advantageously, the method of the invention allows improving a specific near vision power to be provided to a person.

The inventors have found that the providing an ophthalmic lens with the specific near vision power that improves the near vision task processing speed improves the overall comfort of the person.

According to further embodiments which can be considered alone or in combination:
- the method further comprises after the ophthalmic lens providing step a near vision task distance determining step during which a near vision task distance is determined based on the mean power and during the near vision task speed determining step the wearer performs the near vision task at the determined near vision task distance; and/or
- during the near vision task speed determining step the wearer adjusts the near vision distance; and/or
- the ophthalmic lenses provided during the ophthalmic lens providing steps are single vision ophthalmic lenses; and/or
- the near distance is comprised between 25 cm and 60 cm; and/or
- a first at least one ophthalmic lenses provided to the wearer during the first ophthalmic lens providing step has a spherical power corresponding to the wearer's prescription for near vision distance, and when repeating the ophthalmic lens providing step the at least one provided ophthalmic lenses have increasing spherical power one from the other; and/or
- during the near vision task speed determining step the near vision distance corresponds to the inverse of the addition of the wearer's prescription; and/or
- the near vision task speed determining step the near vision distance is adapted by the wearer; and/or
- task processing conditions are the same when repeating the near vision task speed determining step; and/or
- the method further comprises prior to the first near vision task speed determining step a task processing condition determining step during which task processing conditions that minimizes the processing speed of the wearer with a spherical power corresponding to the wearer's prescription for near vision distance is determined and wherein the further near vision task speed determining steps are repeated in such task processing conditions
- the near vision task is a reading task; and/or
- all the texts read by the wearer during the reading speed determining steps have the same contrast value; and/or
- the contrast value is greater than or equal to 11%, for example greater than 14% and smaller than or equal to 100%, for example smaller than or equal to 70%; and/or
- the method further comprises a contrast level determining step during which the contrast resulting in a fall of acuity of 0.1 log MAR relative to the acuity with a contrast of 100% is determined at near distance vision and the reading speed determining steps are carried out with a contrast equal to the determined contrast; and/or
- all the texts read by the wearer during the reading speed determining steps comprise between 5 and 10 words; and/or all the texts read by the wearer during the reading speed determining steps comprise equivalent short and complex sentences; and/or the method further comprises a near vision task speed threshold providing step during which a near vision task speed threshold is provided and the ophthalmic lens providing and the near vision task speed determining steps are repeated until the processing speed is greater or as close as possible to the near vision task speed threshold; and/or the method further comprises a near vision task speed gain providing step during which a near vision task speed gain is provided and the ophthalmic lens providing and the near vision task speed determining steps are repeated until the gain of the processing speed is greater or as close as possible to the near vision task speed gain; and/or the method is applied to determine the specific near vision power of a pair of progressive ophthalmic lenses to be provided to a wearer, wherein a pair of ophthalmic lenses is provided to the wearer at the ophthalmic lens providing step and every further step concerns a pair of ophthalmic lenses; and/or the difference between the specific near vision power and the optical power corresponding to the far vision prescription of the wearer is smaller or equal to 4 Diopters.

The invention further relates to a computer program product comprising one or more stored sequences of instructions that are accessible to a processor and which, when executed by the processor, causes the processor to carry out at least the near vision task speed determining step of the method according to the invention and to determine the specific near vision power.

The invention also relates to a computer-readable storage medium having a program recorded thereon; where the program makes the computer execute at least the near vision task speed determining step of the method according to the invention and to determine the specific near vision power.

The invention further relates to a device comprising a processor adapted to store one or more sequence of instructions and to carry out at least the near vision task speed determining step of the method according to the invention and to determine the specific near vision power.

The invention further relates to an ophthalmic lens ordering system adapted for ordering ophthalmic lenses comprising ordering means adapted for ordering ophthalmic lenses corresponding to the prescription of the wearer comprising at least a near vision zone having a mean power corresponding to a specific near vision power determined by a method according to the invention.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

The invention relates to a method for determining a specific near vision power of an ophthalmic lens to be provided to a wearer having an ophthalmic prescription.

When a presbyopic person expresses discomfort to read the small print the most commonly used solution is to provide progressive lenses with an addition greater than 2.50 D to create the magnification effect but without any justification, questioning or complementary measure.

Such solution is limited by the range of possible addition (2.75, 3.00, 3.25, 3.50) and does not always provide the best benefits.

The idea of the invention is to measure the near distance tasks ability of the wearer, such as reading, and to determine a specific near vision power adapted to the person.

The method of the invention allows determining a specific near vision power of an ophthalmic lens to be provided to a wearer having an ophthalmic prescription, the specific near vision power being for near distance vision.

In the sense of the invention, the prescription is a set of optical characteristics of optical power, of astigmatism and, where relevant, of addition, determined by an ophthalmologist in order to correct the vision defects of an individual, for example by means of a lens positioned in front of his eye. Generally speaking, the prescription for a progressive power lens comprises values of optical power and of astigmatism at the distance-vision point and, where appropriate, an addition value.

Figure 1:
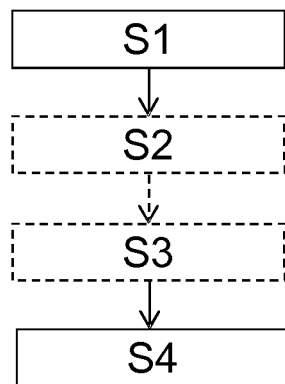
FIG. 1 is a flow chart representing according to the invention.

As illustrated on FIG. 1, the method according to the invention comprises at least:

an ophthalmic lens providing step S1 and a near vision task speed determining step S4.

During the ophthalmic lens providing step S1, an ophthalmic lens having a near vision distance zone comprising a mean power adapted for near vision is provided to the wearer to be tested.

According to an embodiment, the ophthalmic lens provided during the ophthalmic lens providing step S1 is a single vision ophthalmic lens having a single optical power adapted for near vision. Advantageously, providing a single vision ophthalmic lens increases the accuracy of the method of the invention.

In the sense of the invention, the near vision distance corresponds to a distance comprised between 25 cm and 60 cm.

After having provided the ophthalmic lens to the wearer, the wearer is asked to carry out a near vision task while using the provided ophthalmic lens.

In the sense of the invention, a near vision task is a task that requires the wearer's visual attention at a distance comprised between, 25 cm and 60 cm. The near vision task may be whiteout being limited to any of reading, knitting, sewing, writing.

During the near vision task speed determining step S4, the processing speed of a near vision task by the wearer when wearing said provided ophthalmic lens is determined.

The ophthalmic lens providing step S1 and the near vision task speed determining step S4 are repeated with ophthalmic lenses having different mean power, so as to determine a specific near vision power corresponding to the mean power providing an improved near vision task processing speed.

According to an embodiment of the invention, the first ophthalmic lens provided to the wearer during the first ophthalmic lens providing step has a spherical power corresponding to the wearer's prescription for near vision distance. When repeating the ophthalmic lens providing step the provided ophthalmic lenses have increasing spherical power one from the other. Typically, when repeating the ophthalmic lens providing step the spherical power is increased of 0.25 diopters.

As illustrated on FIG. 1, the method may further comprise after the ophthalmic lens providing step S1 a near vision task distance determining step S2.

During near vision task distance determining step S2 a near vision task distance is determined based on the mean power and during the near vision task speed determining step the wearer performs the near vision task at the determined near vision task distance.

For example, during the near vision task speed determining step the near vision distance may correspond to the inverse of the addition of the wearer's prescription.

Alternatively, when carrying out the near vision task the wearer may adjust the near vision task distance.

So as to increase the accuracy of the method, when repeating the near vision task speed determining steps the wearer is asked to carry out the near vision tasks in the same conditions. For example, when reading the type of sentences, the contrast of the text, the size and type of typo are similar.

As illustrated on FIG. 1, the method of the invention may further comprise
prior to the first near vision task speed determining step a task processing condition determining step S3.

During task processing condition determining step S3 task processing conditions that minimizes the processing speed of the wearer with a spherical power corresponding to the wearer's prescription for near vision distance is determined.

The wearer is then asked to carry out the near vision activity in the determined task processing conditions. Advantageously, having the wearer carry out the near vision task in such determined conditions increases the sensitivity of the method of the invention.

According to an embodiment of the invention, the ophthalmic lens providing step and the near vision task speed determining step are repeated until the near vision task speed is increased of a predetermined or specified amount.

For example, the method according to the invention may comprise a near vision task speed gain providing step. During the near vision task speed gain providing step a near vision task speed gain in provided and the ophthalmic lens providing and the near vision task speed determining steps are repeated until the gain of the processing speed is greater or as close as possible to the near vision task speed gain.

For example, the ophthalmic lens providing and the near vision task speed determining steps are repeated until the near vision task speed gain is of 25%.

The method of the invention may further comprise a near vision task speed threshold providing step.

During the near vision task speed threshold providing step a near vision task speed threshold is provided and the ophthalmic lens providing and the near vision task speed determining steps are repeated until the processing speed is greater or as close as possible to the near vision task speed threshold.

For example, the near vision task speed threshold may be of 5 words per second. Therefore, the ophthalmic lens providing and the near vision task speed determining steps are repeated until the near vision task speed gain is of at least 5 words per second.

The invention will be described in greater detailed with reading as a near vision distance task.

For example, sentences are displayed for a given time and the wearer is asked to read the sentences.

Using an adaptive procedure or staircase, the duration of the display of the different sentences is decreased until a minimum display time is reached which allows the wearer to read the displayed sentences. This is equivalent to determining the maximum reading speed of the wearers.

Such arrangement may be used to determine the value of the specific near vision power that improves the reading performance of the wearer by measuring the reading speed at different distances, powers and contrasts.

Figure 2:
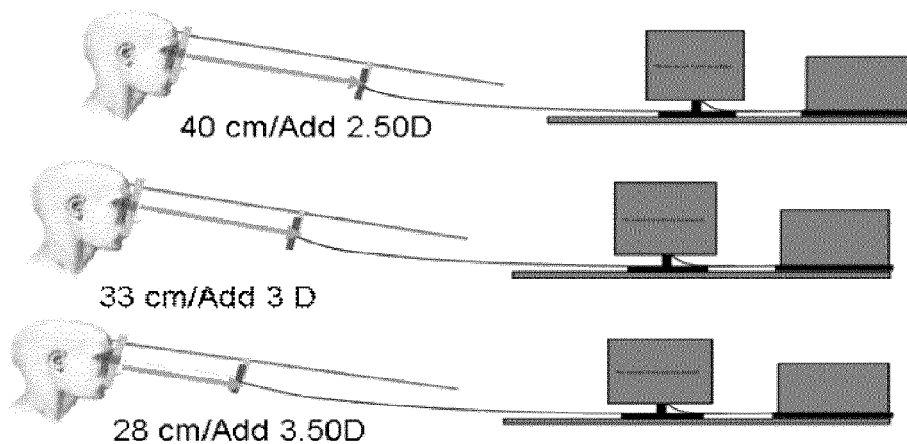
FIG. 2 is a schematic representation of display device that may be used to implement the invention.

The inventors have set up a device for the measurement of the reading speed in near vision with a display device as represented on FIG. 2.

The method uses a sentence generator and determines the threshold of minimum display time required for a wearer to read a sentence.

The sentence generator used in the invention is arranged so that the probability that the displayed sentence is true or false is 50% and allows adapting the display size, the font as well as the contrast.

Preferably, all the texts read by the wearer during the reading speed determining steps comprise equivalent short and complex sentences.

According to an embodiment of the invention, all the texts read by the wearer during the reading speed determining steps have the same contrast value and/or the same font size.

The font used may be Times in size 16, representing an equivalent acuity ranging from 0.14 to 40 cm to 0.29 log MAR to 28 cm.

The display contrasts may range between 10% and 70%. For example, contrast of 70%, 39%, 25%, 14% and 11% have been tested. These contrasts were chosen because they correspond to the contrasts measured on different supports such as newspaper, notices, or magazines.

According to an embodiment of the invention, the method further comprises a contrast level determining step during which the contrast resulting in a fall of acuity of 0.1 log MAR relative to the acuity with a contrast of 100% is determined at near distance vision and the reading speed determining steps are carried out with a contrast equal to the determined contrast.

According to an embodiment of the invention, the method of the invention may further comprise a font size determining step during which a font size of the text displayed to the wearer is determined based on the measurement of the wearer's initial acuity, for example in the contrast conditions used during the method.

For example, during font size determining step the font size resulting in a fall of acuity of 0.1 log MAR relative to the acuity determined for a given contrast and reading distance, typically 40 cm, is determined and the reading speed determining steps are carried out with texts having said determined same font size for all reading distances.

When carrying out the method of the invention one may use a phoropter with the optical power corresponding to the far vision prescription of the wearer and an addition.

The adaptation of the device may be carried out with the idea of recreating a typical reading situation. Thus, the phoropter may be inclined by 22° to force a lowering of the head when reading. The screen itself may be attached to the test bar of the phoropter is therefore perpendicular to the wearer's viewing axis, the centering axis of the lenses cutting off the display of the sentence on the screen. The phoropter may be placed in the convergence position for near vision from the pupillary deviations of the wearer. Thus placed, the wearer can see without moving the head the entire sentence displayed through the phoropter.

Using the method of the invention, the inventors measured the reading speed, i.e. the number of words per second, of 23 senior wearers with 5 different contrasts 70%, 39%, 25%, 14% and 11%. The lens-screen distances that were chosen for the experiment are 40 cm, 33 cm and 28 cm, corresponding to 2.50, 3.00 to 3.50 D additions.

When carrying out the method the inventors displayed of a series of 20 sentences on the screen of the device. The wearer was asked to read the sentences silently. When the sentence was no longer displayed, the wearer was asked to recite the sentence aloud for verification, and the professional carrying out the method could validate whether or not to consider if the sentence was correctly recited. The display time of the sentences varied during the experiment.

The inventors have determined that wearers present in average a greater reading speed for strong contrasts than for the weak. For example: at 40 cm with a contrast of 70% wearers read in average 8 words/second vs. 2 words/second for a contrast of 11% at the same distance.

Furthermore, the inventors have determined that the reading speed improves when reducing the distance and increase the near vision power. For example, at 40 cm with a contrast of 70% wearers read in average 8 words per second vs. 13 words per second in average for a contrast of 70% at 28 cm.

Such results reinforce the approach of the invention to provide a specific near vision power since the wearer gains in speed of reading especially for weak contrasts.

Advantageously, the method of the invention may take into account the wearer's binocular vision and his initial visual acuity.

For example, according to an embodiment of the invention, the method is applied to determine the specific near vision power of a pair of progressive ophthalmic lenses to be provided to a wearer, wherein a pair of ophthalmic lenses is provided to the wearer at the ophthalmic lens providing step and every further step concerns a pair of ophthalmic lenses.

The invention has been described above with the aid of embodiments without limitation of the general inventive concept; in particular the mounted sensing device is not limited to a head mounted device.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining a specific near vision power of an ophthalmic lens to be provided to a wearer having an ophthalmic prescription, the specific near vision power being for near distance vision, the method comprising:
   an ophthalmic lens providing step during which at least an ophthalmic lens having a near distance vision zone comprising a mean power adapted for near distance vision is provided to the wearer,
   a near vision task speed determining step during which the processing speed of a near vision task by the wearer when wearing said provided ophthalmic lens is determined,
   wherein the ophthalmic lens providing step and the near vision task speed determining step are repeated with ophthalmic lenses having different mean power, so as to determine a specific near vision power corresponding to the mean power providing an improved near vision task processing speed, and
   wherein the method further comprises a near vision task speed threshold providing step during which a near vision task speed threshold is provided and the ophthalmic lens providing and the near vision task speed determining steps are repeated until the processing speed is equal or greater to the near vision task speed threshold.

2. The method according to claim 1, wherein the ophthalmic lenses provided during the ophthalmic lens providing steps are single vision ophthalmic lenses.

3. The method according to claim 1, wherein a near distance is comprised between 25 cm and 60 cm.

4. The method according to claim 1, wherein a first at least one ophthalmic lens provided to the wearer during the first ophthalmic lens providing step has a spherical power corresponding to the wearer's prescription for near vision distance, and when repeating the ophthalmic lens providing step the at least one provided ophthalmic lens has increasing spherical power one from the other.

5. The method according to claim 1, wherein during the near vision task speed determining step the near vision distance corresponds to the inverse of the addition of the wearer's prescription, and the prescription is a prescription for a progressive power lens.

6. The method according to claim 1, wherein the near vision task speed determining step the near vision distance is adapted by the wearer.

7. The method according to claim 1, wherein during the repetition of the near vision task speed determining step, task processing conditions are the same for each provided ophthalmic lens.

8. The method according to claim 1, wherein the method further comprises prior to the first near vision task speed determining step a task processing condition determining step during which task processing conditions that minimizes the processing speed of the wearer with a spherical power corresponding to the wearer's prescription for near vision distance is determined and wherein the further near vision task speed determining steps are repeated in such task processing conditions.

9. The method according to claim 1, wherein the near vision task is a reading task.

10. The method according to claim 9, wherein all the texts read by the wearer during the reading speed determining steps have a same contrast value and/or a same font size.

11. The method according to claim 10, wherein the contrast value is greater than or equal to 11% and smaller than or equal to 100%.

12. The method according to claim 9, wherein the method further comprises a contrast level determining step during which the contrast resulting in a fall of acuity of 0.1 log MAR relative to the acuity with a contrast of 100% is determined at near distance vision and the reading speed determining steps are carried out with a contrast equal to the determined contrast.

13. The method according to claim 9, wherein all the texts read by the wearer during the reading speed determining steps comprise between 5 and 10 words.

14. An ophthalmic lens ordering system adapted for ordering ophthalmic lenses comprising ordering means adapted for ordering ophthalmic lenses corresponding to the prescription of the wearer comprising at least an ophthalmic lens having a near vision zone, said near vison zone having a mean power corresponding to a specific near vision power determined by a method according to claim 1.

15. The method according to claim 2, wherein a near distance is comprised between 25 cm and 60 cm.

16. The method according to claim 2, wherein a first at least one ophthalmic lens provided to the wearer during the first ophthalmic lens providing step has a spherical power corresponding to the wearer's prescription for near vision distance, and when repeating the ophthalmic lens providing step the at least one provided ophthalmic lens has increasing spherical power one from the other.

17. The method according to claim 3, wherein a first at least one ophthalmic lens provided to the wearer during the first ophthalmic lens providing step has a spherical power corresponding to the wearer's prescription for near vision distance, and when repeating the ophthalmic lens providing step the at least one provided ophthalmic lens has increasing spherical power one from the other.

18. The method according to claim 2, wherein the near vision task speed determining step the near vision distance is adapted by the wearer.

19. The method according to claim 3, wherein the near vision task speed determining step the near vision distance is adapted by the wearer.

20. The method according to claim 10, wherein the contrast value is greater than 14%.

21. The method according to claim 10, wherein the contrast value is smaller than or equal to 70%.

* * * * *